United States Patent [19]

Strimling et al.

[11] Patent Number: 5,211,659
[45] Date of Patent: May 18, 1993

[54] PUMP SYSTEM SUITABLE AS A HEART ASSIST DEVICE

[76] Inventors: Walter E. Strimling, 79 Jericho Rd., Weston, Mass. 02193-1209; Francis A. DeBernardis, Jr., 352 Hillcrest Rd., Ridgewood, N.J. 07450; Herbert M. Shapiro, 92 Chelsea Way, Bridgewater, N.J. 08807

[21] Appl. No.: 609,388

[22] Filed: Nov. 5, 1990

[51] Int. Cl.⁵ .......................................... A61M 11/10
[52] U.S. Cl. .......................................... 623/3; 600/16
[58] Field of Search ...................... 623/3; 600/16, 17

[56] References Cited

U.S. PATENT DOCUMENTS

| 4,512,726 | 4/1985 | Strimling | 623/3 |
| 4,902,291 | 2/1990 | Kolff | 623/3 |
| 4,976,730 | 12/1990 | Kwan-Gett | 623/3 |

Primary Examiner—David Isabella
Attorney, Agent, or Firm—Herbert M. Shapiro

[57] ABSTRACT

Artificial heart type devices are made into practical heart assist devices by making the blood chambers of the device disposable or by adapting the blood chambers to accept disposable inserts. The inserts have extensions which protrude through the inlet and outlet ports of the chambers to connect to the blood system of a living body.

9 Claims, 3 Drawing Sheets

PUMP SYSTEM SUITABLE AS A HEART ASSIST DEVICE

FIELD OF THE INVENTION

This invention relates to disposable pump systems and more particularly, to such systems which can be attached to the human body and can be used as a heart assist device for prolonged periods.

BACKGROUND OF THE INVENTION

There is a class of medical emergencies for which little, if anything, can be done for the patient. A patient's heart ceases to beat and heroic efforts are undertaken by medical professionals to revive the patient. Very little time elapses before irreparable damage is done to vital organs. These situations occur in operating rooms, in intensive care facilities, and in emergency rooms.

In the operating room, a heart-lung machine may be used to perform heart functions while heart operations are conducted. But such machines cause damage to the blood and can be used only for relatively short periods of time.

Artificial hearts are well known also. But such hearts are only for experimental purposes for implantation, when a human heart no longer performs its critical function of pumping blood to vital organs and has to be replaced or the patient dies. Artificial hearts are designed for internal use and are expensive. Moreover they cause blood clots and infection problems which are as yet unresolved. If no biological heart is available, there is no long term support for the patient except such implantable devices. Available short term pumping devices are approved for use for up to 6 hours and are not designed to be replacement devices for intermediate use for providing the pumping function equal to that of the natural heart. Such short term devices provide only minor support for the heart and do not respond to needs for perfusion nor for meeting human physiological needs.

A variety of heart assist devices is also available. But these devices also have problems. They cause damage to the blood, require the heart to work harder, and also, in some instances, cause clots.

U.S. Pat. No. 4,547,911 issued Oct. 22, 1985 to W. E. Strimling discloses an implantable heart pump which needs no external vent. Because most infections in such devices originate from such a vent, a prime source of infection is eliminated. U.S. Pat. No. 4,468,177 issued Aug. 28, 1984 and U.S. Pat. No. 4,512,726 issued Apr. 23, 1985 disclose implantable heart pumps where the blood chambers are designed to eliminate crevices which produce clotting and the pump motors are driven in a manner to reduce damage to the blood.

In the pump disclosed in the above-mentioned patents and, as is the case in all implantable hearts and heart assist devices, a blood chamber in the device is equiped with inlet and outlet ports operative to admit blood into the chamber when the volume of the chamber is increased and to vacate the chamber when the volume of the chamber is reduced. In the above mentioned patents, the volume of the blood chamber is changed by a motor-driven pusher plate which moves up and down against the bottom of the chamber. A left ventrical assist device would be operative in this manner.

The patents also describe placing the motor and drive mechanism in a chamber located between two blood chambers. Such a device includes two pusher plates operative out of phase with one another. Thus, the volume of one blood chamber decreases while the volume of the other increases. Such an arrangement is useful as a heart replacement.

BRIEF DESCRIPTION OF ILLUSTRATIVE EMBODIMENTS OF THIS INVENTION

In accordance with the principles of this invention, a heart assist device is provided for quick attachment to the body of, say, an accident victim, or, for example, a patient having heart failure during an operation. The device can be used for days without risk of damage to the heart thus allowing the surgeon time to consider less than the most heroic measures.

The invention is based on the recognition that many medical procedures could be carried out in comparative safety if a reliable and relatively inexpensive "heart" could be substituted for the human heart for an extended period. Perhaps even more important, many patients too weak to be suitable candidates for surgery could be operated on if such a device were available.

In a preferred embodiment, the blood chambers of the devices of the above-identified patents include a locking device to disconnect the blood chamber housings from the pump chamber housing so that the blood chamber housings can be disposed of. New blood chamber housings are connected for a new patient. The inlet and outlet ports are connected to cannulas for connection to, for example, the femoral artery and vein.

In another embodiment, the top portion of each blood chamber housing is hinged and an insert conforming to the interior surface of the housing is inserted into each. The insert has extensions which protrude through the inlet and outlet ports and are connected to cannulae. The hinged housing can be made like a vacuum chuck to insure that the insert is free of crevices.

It is believed that the adaptation of human heart replacements, as yet unfit for sale, as disposable heart assist devices for short term use outside the body, represents a significant departure from prior art thinking.

DETAILED DESCRIPTION OF ILLUSTRATIVE EMBODIMENTS OF THIS INVENTION

Figure 1:
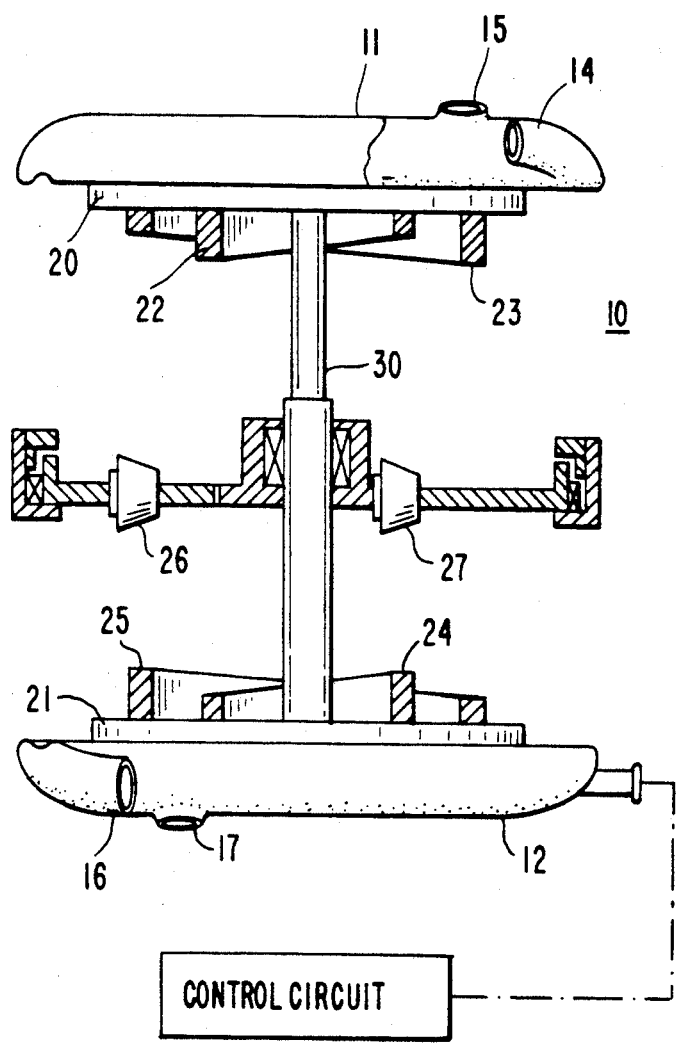
FIG. 1 is a schematic representation of a prior art artificial heart adaptable for use in accordance with the principles of this invention.

FIG. 1 shows a prior art artificial heart 10 as disclosed in the above-identified patents which are specifically incorporated herein by reference. The heart contains first and second hollow housings 11 and 12 which define blood chambers therein. The housings include inlet and outlet ports 14 and 15 and 16 and 17 for housings 11 and 12, respectively.

Pusher plates 20 and 21 form the bottom and top surfaces of the housings 11 and 12 as viewed in the figure. Ramps 22 and 23 and 24 and 25 are mounted on pusher plates 20 and 21 respectively. Rollers 26 and 27 engage the ramps and move the pusher plates up and down in a manner to alternately reduce and expand the volume of the blood chambers defined by the housings as disclosed fully in the above-noted patents. Movement of the pusher plates is constrained to an axis defined by piston 30.

Figure 2:
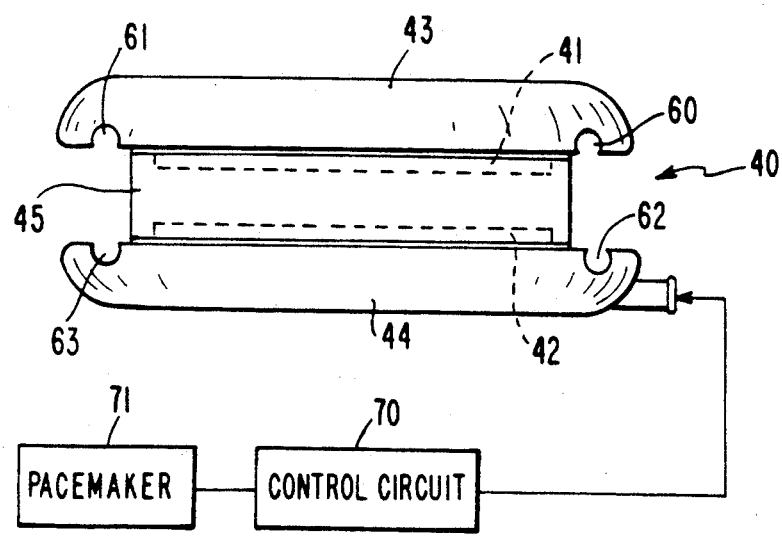
FIG. 2 is a schematic representation of the artificial heart of FIG. 1 adapted in accordance with the principles of this invention.
Figure 3:
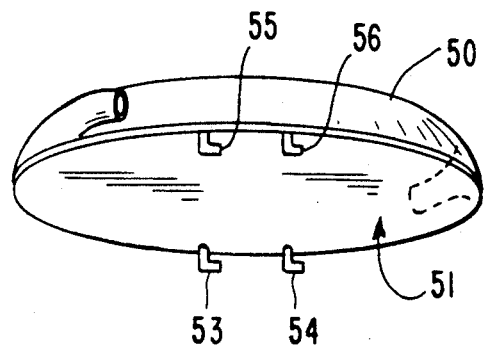
FIGS. 3, 4, and 6 are schematic representations of alternative blood chamber housing configurations for the artificial heart of FIG. 2.

FIG. 2 shows an arrangement 40 similar to that of FIG. 1 but distinguished by several critical differences. Firstly, the pusher plates 41 and 42 are not attached to the blood chamber housings 43 and 44, respectively. Secondly, housings 43 and 44 are removable from the pump chamber housing therebetween. The manner in which the blood chamber housing connects to the pump chamber housing may vary. If the blood chamber housing is to be disposable, it is made of structurally-stable, bio-compatable material such as Nylon. Each blood chamber housing is made hollow having a rigid top portion 50 and a flexible bottom portion 51 as shown in FIG. 3. The bottom portion is adapted, illustratively, with conventional locking members 53, 54, 55, and 56 to insert into mating slots (not shown) in the surface of the pump chamber housing. The locking members may be located on the pump chamber housing with mating slots located on the blood chamber housing. Alternatively, the blood chamber housing may be threaded in a conventional manner to screw into a pump chamber housing having mating female screw threads (not shown).

The inlet and outlet ports 60 and 61 or 62 and 63 can be located as shown in FIG. 1 or located as shown in FIG. 2. For disposable blood chamber housings, the locations of the ports are not critical for heart assist devices for use outside of the body.

The inlet and outlet ports, in all embodiments herein are equipped with leaf (tricuspid) valves (not shown) so that the device is pulsatile. The device, moreover, is free of crevices and is operated in a manner to reduce the pressure in the heart and to initiate a blood chamber volume reduction relatively slowly rather than as a step function to reduce damage to the blood. These functions are controlled by a control circuit 70 responsive to signals, for example, from a pace maker 71 connected to the patient. In the absence of a functioning heart, the control circuit is responsive to signals generated under microprocessor control according to an algorithm which mimics a normal pace maker response.

Figure 4:
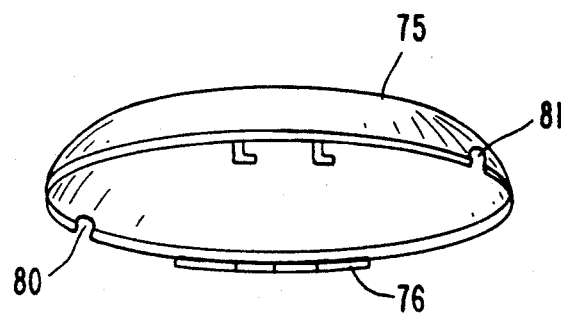

The positions of the inlet and outlet ports are preferably at the edge of the blood chamber housing in the embodiment of FIG. 4. In this embodiment, the blood chamber housing has only a top portion corresponding to portion 50 of FIG. 3. There is no bottom portion in this embodiment to correspond to portion 51 of FIG. 3. The blood chamber housing of FIG. 4 is not really a blood chamber. Instead it is a holder hinged to the pump chamber housing by hinge 76. The holder includes locking members to secure the holder to the pump chamber housing by insertion into mating slots with spring bias latches (not shown) which are conventional.

Figure 5:
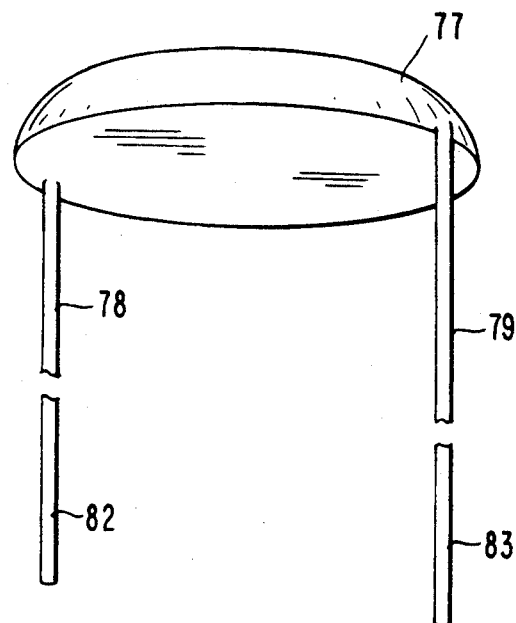
FIG. 5 is a blood compatable insert with extensions for use in the blood chamber housings of the type shown in FIGS. 3, 4, and 6

A holder of the type shown in FIG. 4 is adapted to hold a balloon-shaped blood chamber 77 as shown in FIG. 5. The blood chamber is equipped with extensions 78 and 79 positioned to extend through inlet and outlet ports 80 and 81 when the holder is closed. Thus, it is clear that the inlet and outlet ports are conveniently located along the bottom edge of the holder in this embodiment.

It should also be clear that a holder of FIG. 4 need not be of any particular material nor need it be solid. Such a holder could be a rigid screen of the conforming shape. Thus, it should be clear that the pump assembly and pump chamber housing along with the control circuitry represents the major expense in such a pump system. The blood chamber housings are disposable or are adapted to receive disposable blood chambers as shown in FIG. 5.

In any case, the inlet and outlet ports are intended for connection to the blood system of the human body. This is accomplished, for example, by connection to the femoral artery and vein, respectively. The connection is made by the use of cannulae represented at 82 and 83 in FIG. 5. Although cannulae are in common use, extensions 78 and 79 could be terminated in the form of cannulae for facilitating use.

The blood chamber of FIG. 5 may be supplied slightly inflated with, for example, removable caps (not shown) in place over the distal ends of extensions 78 or 79 or over the distal ends of cannulae 82 or 83. A slightly inflated chamber would be easier to position into a holder of FIG. 4.

Figure 6:
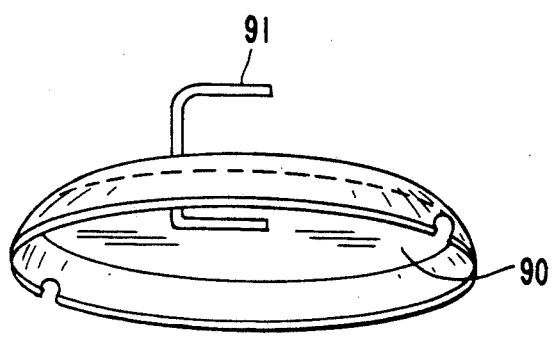

FIG. 6 shows a holder 89 of the type shown in FIG. 4 with an additional diaphragm 90 in the upper portion of the holder. An arm 91 is turned to move the diaphragm upwards in the manner of a vacuum chuck to help position the blood chamber of FIG. 5. The handle is turned to a release position when the pump procedure is terminated.

A pump system in accordance with the principles of this invention is intended to serve as a heart assist device for use outside of the human body. The pump drive regimen and blood chamber housing configurations are designed to provide no crevices for formation of blood clots, to be pulsatile, and to initiate a pumping cycle relatively slowly so as to mimic a normal heart performance as mentioned above. The heart assist device also can be adjusted to reduce the blood content of the normal heart operating in series with it to reduce the work done by the heart.

But the system also is intended to substitute for the normal heart and to do so for extended periods of days rather than for the limited time to which prior art devices have been restricted. The operation and control of a pump suitable for use in accordance with the principles of this invention are described in the above mentioned U.S. patents. Copending application Ser. No. 560,117 filed Aug. 31, 1990, now U.S. Pat. No. 5,133,743 for W. E. Strimling, a coinventor of the present invention, discloses further improvements in the pump drive regimen for pump systems of the type disclosed.

What is claimed is:

1. A heart assist device for use outside the human body, said device including a first rigid housing defining a first blood chamber having a mean volume, said device including at least a second rigid housing defining a pump chamber, said first rigid housing including inlet and outlet ports, said second rigid housing including means for alternately increasing and decreasing the volume of said first blood chamber, said device including means for opening said first rigid housing with respect to said second rigid housing for accepting a disposable conformable insert therein, said device including said insert, said insert being shaped to conform to said first blood chamber and including first and second elongated extensions extend therefrom and configured to extend through said inlet and outlet ports respectively for use with first and second cannulae respectively.

2. A device as set forth in claim 1 also including a third housing for defining a second blood chamber, said third housing also including inlet and outlet ports and a second disposable conformable insert, said second disposable insert including first and second elongated extensions for use with associated cannalae.

3. A device as set forth in claim 1 wherein said first and second inserts are of a blood compatible material.

4. A device as set forth in claim 2 wherein said inserts are of blood compatible material.

5. A device as set forth in claim 1 wherein said first rigid housing is hinged to said second rigid housing for accepting said insert.

6. A device as set forth in claim 2 wherein said first and third housings are detachable to said second housing for accepting said inserts.

7. A heart assist device as set forth in claim 1, wherein said first rigid housing has an inner surface, said insert having a shape to conform to said inner surface of said first rigid housing.

8. A device as set forth in claim 1 wherein said second housing is structurally stable, said second housing including means for creating a vacuum in a manner to secure said conforming insert to the interior surface thereof.

9. A device as set forth in claim 2 wherein each of said second and third housings is structurally stable, said housings including means for creating a vacuum in a manner to secure the associated one of said inserts to the interior surface thereof.

* * * * *